(12) United States Patent
Azpiroz et al.

(10) Patent No.: US 11,906,515 B2
(45) Date of Patent: *Feb. 20, 2024

(54) MULTIPLEXED LATERAL FLOW ASSAY DEVICE

(71) Applicants: INTERNATIONAL BUSINESS MACHINES CORPORATION, Armonk, NY (US); FUNDACAO OSWALDO CRUZ, Rio de Janeiro (BR)

(72) Inventors: Jaione Tirapu Azpiroz, Rio de Janeiro (BR); Ademir Ferreira da Silva, Sao Paulo (BR); Matheus Esteves Ferreira, Rio de Janeiro (BR); Ricardo Luis Ohta, Sao Paulo (BR); Mathias B. Steiner, Rio de Janeiro (BR); Antonio Gomes Pinto Ferreira, Rio de Janeiro (BR); Edimilson Domingos da Silva, Rio de Janeiro (BR); Nara Mazarakis Rubim, Rio de Janeiro (BR); Pedro Paulo Ferreira Ribeiro, Rio de Janeiro (BR)

(73) Assignees: INTERNATIONAL BUSINESS MACHINES CORPORATION, Armonk, NY (US); FUNDACAO OSWALDO CRUZ, Rio de Janeiro (BR)

( * ) Notice: Subject to any disclaimer, the term of this patent is extended or adjusted under 35 U.S.C. 154(b) by 439 days.

This patent is subject to a terminal disclaimer.

(21) Appl. No.: 16/845,035

(22) Filed: Apr. 9, 2020

(65) Prior Publication Data
US 2020/0376485 A1  Dec. 3, 2020

Related U.S. Application Data

(63) Continuation-in-part of application No. 16/428,961, filed on May 31, 2019, now Pat. No. 11,549,943.

(51) Int. Cl.
*G01N 33/543* (2006.01)
*B01L 3/00* (2006.01)
*G01N 33/571* (2006.01)

(52) U.S. Cl.
CPC .... *G01N 33/54389* (2021.08); *B01L 3/50273* (2013.01); *B01L 3/502715* (2013.01);
(Continued)

(58) Field of Classification Search
CPC ............ G01N 30/02; G01N 2030/027; G01N 2035/00108; G01N 2021/7759;
(Continued)

(56) References Cited

U.S. PATENT DOCUMENTS 4,366,241 A * 12/1982 Tom ..................... G01N 33/558
435/5
5,108,889 A * 4/1992 Smith ................ A61B 5/15113
435/7.1
(Continued)

FOREIGN PATENT DOCUMENTS

EP       1473565 A1    11/2004
WO   2015200316 A1    12/2015

OTHER PUBLICATIONS

List of IBM Patents or Patent Applications Treated as Related, 2 pgs.
(Continued)

*Primary Examiner* — Christopher L Chin
(74) *Attorney, Agent, or Firm* — Intelletek Law Group, PLLC; Gabriel Daniel, Esq.

(57) ABSTRACT

A multiplexed lateral flow device includes an impermeable internal reservoir having an opening to receive a sample deposition. A fluid distributor pad is arranged in fluid communication with a lower surface of the internal reservoir. The fluid distributor pad includes a paper based micro-
(Continued)

fluidic element having a pattern of a hydrophobic material to distribute a portion of the sample deposition substantially equally among a plurality of flow paths. Lateral flow assays having a plurality of flow lines are aligned with flow paths of the distributor pad. An impermeable top cover has a first window arranged over the opening of the internal reservoir, and at least a second window arranged over the test results of the lateral flow assays. A housing element houses the reservoir, the distributor pad and lateral flow assays. The housing element includes an impermeable bottom cover and a spacer element arranged between the top and bottom covers and, provides a gap between the lateral flow assays and the impermeable top cover.

15 Claims, 13 Drawing Sheets

(52) U.S. Cl.
CPC ........ *G01N 33/571* (2013.01); *B01L 2200/10* (2013.01); *B01L 2300/0816* (2013.01); *B01L 2300/0867* (2013.01); *B01L 2400/0487* (2013.01)

(58) Field of Classification Search
CPC . G01N 2035/00019; G01N 2201/0256; G01N 33/558; G01N 33/4875; G01N 33/54386; G01N 33/54388; G01N 33/54389; G01N 33/536; G01N 33/5302; G01N 33/54387; B01L 2300/0825; B01L 2300/0829; B01L 2300/0861; B01L 2300/0864; B01L 2300/126

USPC .... 435/7.2, 803, 286.5, 287.1, 287.8, 287.9, 435/288.2, 288.3, 970; 935/111; 436/16, 436/46, 541, 514, 169, 520; 422/68.1, 422/70, 417, 421, 425, 429, 430, 551, 422/552, 565, 566, 569, 502, 503, 504, 422/507

See application file for complete search history.

(56) References Cited

U.S. PATENT DOCUMENTS

| | | | |
|---|---|---|---|
| 9,335,290 B2 | 5/2016 | Ewart et al. | |
| 9,784,734 B2 | 10/2017 | Esfandiari | |
| 2009/0263854 A1* | 10/2009 | Jacono | G01N 33/558 156/313 |
| 2012/0003727 A1 | 1/2012 | Esfandiari | |
| 2013/0161190 A1 | 6/2013 | Ewart et al. | |
| 2016/0025715 A1* | 1/2016 | DiMagno | G01N 27/3272 506/9 |
| 2016/0258943 A1 | 9/2016 | Esfandiari | |
| 2017/0219573 A1 | 8/2017 | Needham et al. | |
| 2017/0234866 A1 | 8/2017 | Hamad-Schifferli et al. | |
| 2018/0372755 A1 | 12/2018 | Gehrke et al. | |
| 2019/0064162 A1 | 2/2019 | Esfandiari et al. | |

OTHER PUBLICATIONS

Hu, J. et al., "Advances in Paper-Based Point-of-Care Diagnostics" Biosensors and Bioelectronics (2014); vol. 54; pp. 585-597.
Li, X. et al., "A Perspective on Paper-Based Microfluidics: Current Status and Future Trends"; Biomicrofluidics (2012); vol. 6:011301; 13 pgs.

* cited by examiner

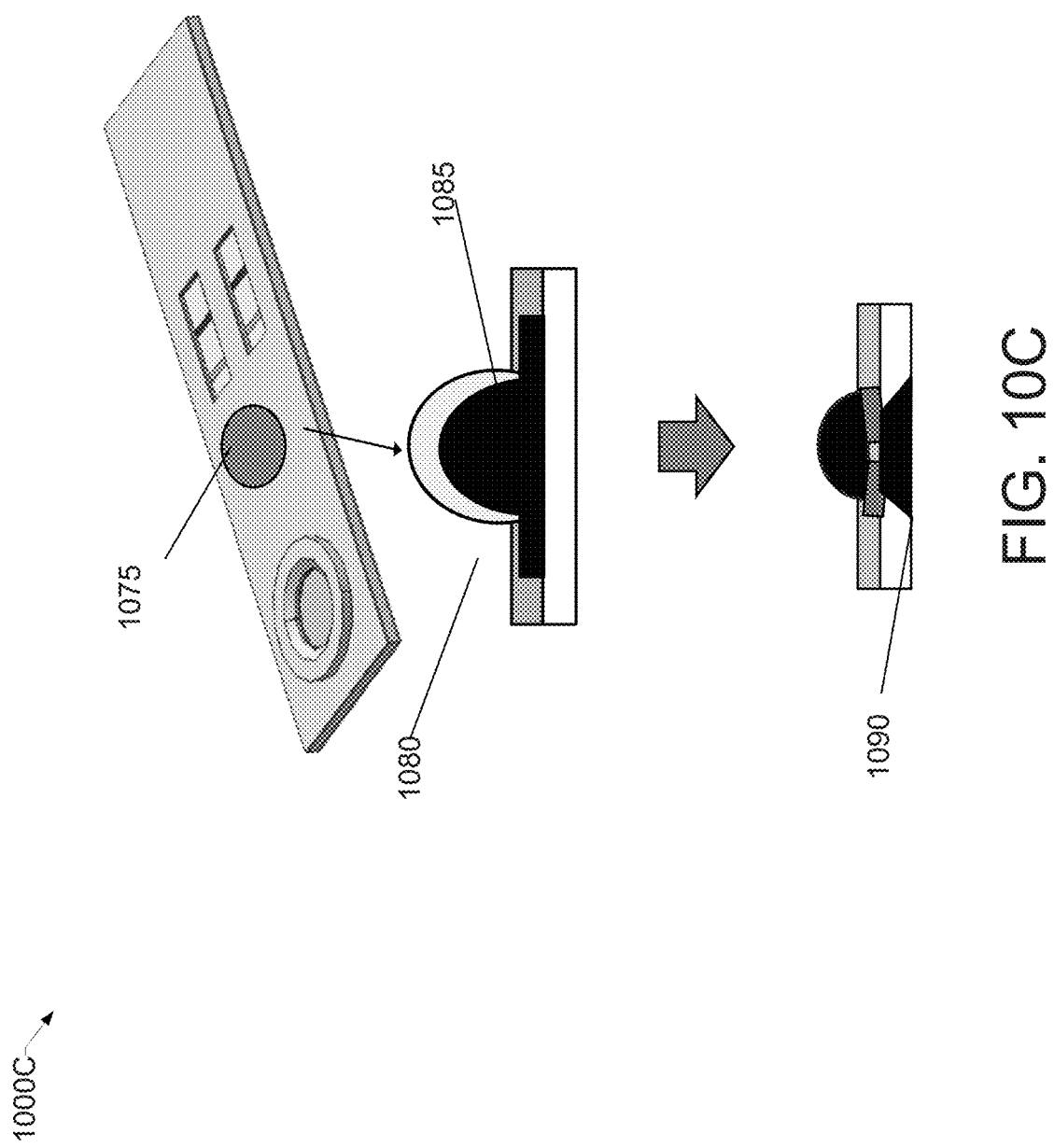

MULTIPLEXED LATERAL FLOW ASSAY DEVICE

BACKGROUND

Technical Field

The present disclosure generally relates to rapid testing using assays, and more particularly, to rapid diagnostic testing using immunoassays.

Description of the Related Art

Rapid testing is increasing in popularity for a number of reasons including low cost, overall accuracy, and the ability to perform an assay test in a remote area. In addition, the results are often obtained in less than 30 minutes. Immunochromatographic lateral flow assays, herein after referred to as lateral flow assays, are a type of rapid test in which a sample is directed to flow through a hydrophillic paper and reacts with one or more reagents embedded in the path of the sample's flow.

SUMMARY

According to various embodiments, a multiplexed lateral flow device and a method of manufacture are provided. A multiplexed lateral flow device includes an impermeable internal reservoir having a body with an upper surface, a lower surface, and an opening in the body to receive a sample deposition. A fluid distributor pad is arranged in fluid communication with a lower surface of the internal reservoir. The fluid distributor pad includes a paper based microfluidic element having a pattern of a hydrophobic material to distribute the sample deposition substantially equally among the plurality of flow paths. Two or more lateral flow assays, have a plurality of flow lines arranged in fluid communication with the plurality of flow paths of the fluid distributor pad.

An impermeable top cover has a first window arranged over the opening of the internal reservoir, and at least a second window arranged over a test result of the lateral flow assays. An impermeable bottom cover opposes the impermeable top cover, and an impermeable housing element is arranged between the impermeable top cover and bottom cover. The fluid distributor pad and the two or more lateral flow assays are arranged within the housing element, and the housing element is configured to provide a gap between the two or more lateral flow assays and the impermeable top cover.

The distributor pad is configured to divide a portion of the sample deposition in the internal reservoir substantially equally among a plurality of flow paths. Two or more lateral flow assays having a plurality of flow lines are arranged in fluid communication with the distributor pad. The two or more lateral flow assays include a test result portion and a control portion for each assay test.

In one embodiment, an impermeable top cover includes a first window arranged over the opening of the internal reservoir. At least a second window is arranged over the test results. A housing element comprising an impermeable bottom cover and an impermeable spacer element is arranged below the impermeable cover. The spacer element, arranged between the top and bottom covers, is configured to house the internal reservoir, the distributor pad and the two or more lateral flow assays and to provide a gap between the two or more lateral flow assays and the impermeable top cover.

In an embodiment, the test results exposed by the second window include a test portion and a control portion of the lateral flow assays.

In one embodiment, the fluid distributor pad is formed of a paper having a pattern of a hydrophobic material to distribute the sample depositions substantially equally among the plurality of flow paths.

In one embodiment, the internal reservoir is configured to receive a sample volume of a liquid, and to retain decreasing portions of the sample volume over a predetermined range of time equal to or greater than a time during which the liquid is being wicked into the fluid distributor pad.

In one embodiment, the predetermined range of time in which the sample volume of the liquid is retained by the internal reservoir is based on at least a viscosity of the liquid or a rate at which the fluid distributor pad wicks the liquid or a wicking rate of the fluid distributor pad.

In one embodiment, the multiplexed lateral flow device includes a plurality of strategic pressure elements arranged between the impermeable top cover and an upper portion of the lateral flow assays. The strategic pressure elements are laterally arranged to increase contact pressure at predetermined interfaces of the two or more lateral flow assays.

In one embodiment, a plurality of lateral flow assays is respectively configured to perform different assay tests, or a repetitive assay test, at the same time. The spacer element includes one or more partitioning strips that isolate each one of the plurality of lateral flow assays housed by the spacer element. The partitioning strips provide a gap between the plurality of lateral flow assays and the impermeable top cover.

According to one embodiment, a multiplexed multiple lateral flow device includes an internal reservoir having a body with an upper surface, a lower surface, and an opening in the body to receive a sample deposition. A multi-layer fluid distributor pad is arranged in fluid communication with the internal reservoir. The multi-layer fluid distributor pad includes a top layer, a bottom layer, and an inner layer having a hydrophobic wax-filled area. A hydrophilic paper channel communicates with a plurality of flow paths configured to distribute substantially equally at least a portion of the sample deposition in the internal reservoir among the plurality of flow paths. A plurality of lateral flow assays having flow lines that are aligned with the plurality of flow paths of the multi-layer fluid distributor pad.

In one embodiment, a housing element comprises an impermeable bottom cover and an impermeable spacer element. The spacer element houses the plurality of lateral flow assays, and the spacer element includes one or more partitioning strips arranged to isolate each of the plurality of lateral flow assays housed by the spacer element. The spacer element also includes an un-partitioned area for the arrangement of the internal reservoir and the fluid distributor pad in alignment with the two or more lateral flow assays. An impermeable top cover has a first window arranged over the opening of the internal reservoir, and at least a second window arranged over a test result portion and a control portion of each of the lateral flow assays. The housing element is arranged below the impermeable top cover to position the spacer element between the impermeable top cover and the impermeable bottom cover.

In one embodiment, the internal reservoir is integrated with a control portion and a distribution portion of the inner layer of the multi-layer fluid distributor pad for a horizontally arranged structure of the inner layer.

In one embodiment, the internal reservoir is integrated with a control portion and a distribution portion of the inner layer of the multi-layer fluid distributor pad for a vertically arranged structure of the inner layer.

In one embodiment, the multi-test device is configured to test simultaneously for a presence of multiple analytes of interest, using a single sample deposition.

In one embodiment, the multiplexed lateral flow device is configured to test for the presence of analytes of interest in bodily fluids including saliva, whole blood, blood plasma, or urine.

In one embodiment, the multiplexed lateral flow device is configured to test for the presence of analytes in the fluid sample conducive to a diagnosis of diseases including HIV (human immunodeficiency virus), syphilis, dengue, tuberculosis and more. There may be biomarkers configured to perform treatment monitoring tests on one or more of HIV, syphilis, dengue or tuberculosis.

In one embodiment, the internal reservoir, the spacer element, the pressure point elements and the impermeable top and bottom covers are all made of paper or other disposable material.

According to one embodiment, a method of manufacturing a multiplexed lateral flow device includes providing an impermeable internal reservoir having a body with an upper surface, a lower surface, and an opening in the body to receive a sample deposition. A fluid distributor pad is arranged in fluid communication with a lower surface of the internal reservoir. The distributor pad is configured to divide a portion of the sample deposition from the internal reservoir among a plurality of flow paths. A pattern of a hydrophobic material is provided on the distributor pad to distribute the sample. Two or more lateral flow assays having the plurality of flow paths in fluid communication are aligned with the distributor pad, the two or more lateral flow assays including a test result for each assay test. A housing element is provided comprising an impermeable bottom cover and an impermeable spacer element, the spacer element including one or more partitioning strips arranged to isolate each of the plurality of lateral flow assays housed by the spacer element, and an un-partitioned area for the arrangement of the internal reservoir and fluid distributor pad. The plurality of lateral flow assays is positioned within the housing element separated by the partitioning strips, in fluid communication with the fluid distributor pad and the internal reservoir positioned in the housing element un-partitioned area. An impermeable paper top cover is positioned over the housing element lodging the two or more lateral flow assays, the distributor pad and the internal reservoir.

The impermeable top cover has a first window arranged over the opening of the internal reservoir, and at least a second window arranged over the test results of the lateral flow assays.

In one embodiment, a plurality of strategic pressure elements is arranged between the impermeable top cover and an upper portion of the lateral flow assays. The sample deposition is divided from the internal reservoir substantially equally among a plurality of flow paths.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

FIGS. 10A, 10B, and 10C show a multiplexed lateral flow device having an integrated buffer container, consistent with an illustrative embodiment.

DETAILED DESCRIPTION

In the following detailed description, numerous specific details are set forth by way of examples to provide a thorough understanding of the relevant teachings. However, it should be apparent that the present teachings may be practiced without such details. In other instances, well-known methods, procedures, components, have been described at a relatively high-level, without detail, to avoid unnecessarily obscuring aspects of the present teachings.

Figure 1A:
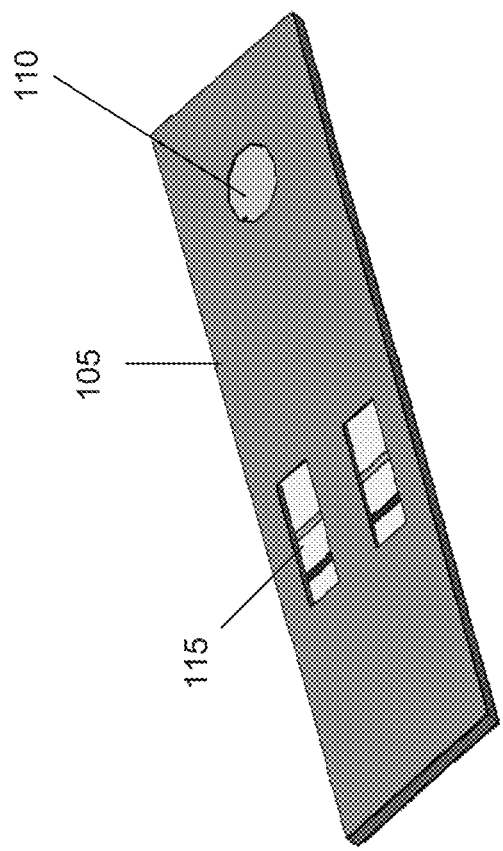
FIG. 1A is a perspective view of a multiplexed lateral flow device, consistent with an illustrative embodiment.

In one aspect, the present disclosure relates to a multiplexed lateral flow device having multiple lateral flow assays. FIG. 1A illustrates in 100A a perspective view of a multiplexed lateral flow device, consistent with an illustrative embodiment. A top cover 105 has openings (e.g., windows) for a sample deposition to perform the test, and to display the test results. For example, the sample deposition opening 110 is shown in this embodiment as being arranged in the top cover 105 over a reservoir that retains the sample. The test result windows 115 show the results of respective assay tests. While FIG. 1A shows a sample deposition opening 110 that is circular, this embodiment is not limited to any particular shape. For example, the sample deposition opening can be square, rectangular, triangular, oblong, irregularly shaped, etc. Similarly, FIG. 1A shows two test results in windows 115 because this multiplexed lateral flow assay includes two assays. However, there can be larger quantities of lateral flow assays, and there may be a test result window 115 for each lateral flow assay, respectively. Alternatively, or in addition, there may be a single test result window sufficiently large to display the test results of multiple lateral flow assays.

Figure 1B:
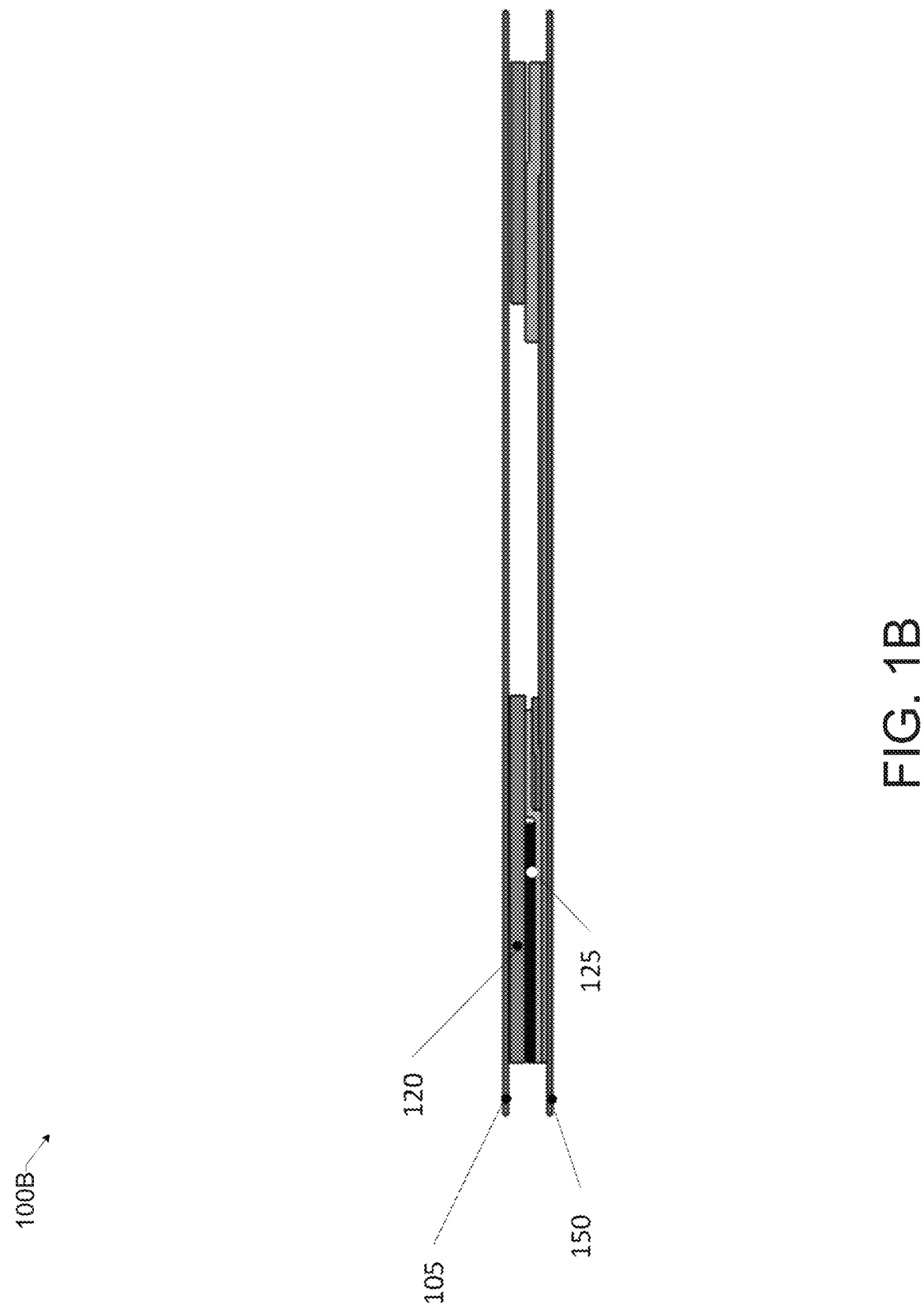
FIG. 1B is a side view of the multiplexed lateral flow device of FIG. 1A.

FIG. 1B illustrates a side view 100B of the multiplexed lateral flow assay shown in FIG. 1A. There is a top cover 105, a bottom cover 150, an internal reservoir 120, and a fluid distributor pad 125.

Figure 2:
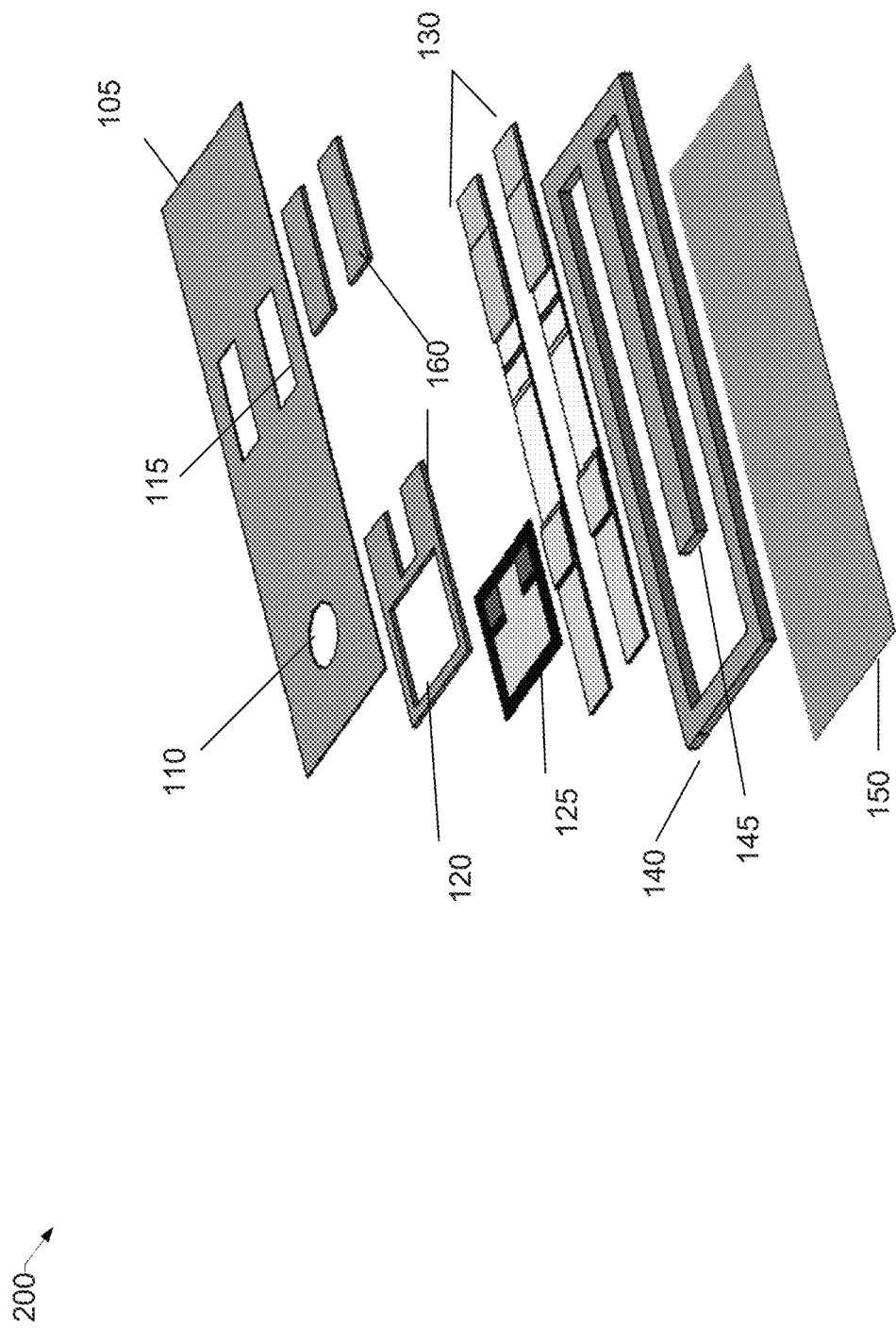
FIG. 2 is an exploded view of a multiplexed lateral flow device, consistent with an illustrative embodiment.

FIG. 2 is an exploded view 200 of a multiplexed lateral flow device, consistent with an illustrative embodiment. In this embodiment, the top cover 105 and bottom cover 150 are formed of a paper that has a hydrophobic coating so as to be impermeable to the sample and buffer solution.

Internal reservoir 120 has a body with an upper surface, a lower surface, and an opening in the body to receive a sample deposition. In addition, the internal reservoir 120 is configured to receive an expected sample volume of liquid at once, (e.g., a predetermined volume of ul) and to retain the sample volume for a period while the liquid is being wicked into a fluid distributor pad 125. As the liquid is being wicked into the fluid distributor pad 125, the portion of the sample in the internal reservoir decreases over the wicking time.

For example, the internal reservoir is configured to receive a sample volume of a liquid, and to retain decreasing portions of the sample volume over a predetermined range of time equal to or greater than a time during which the liquid is being wicked into the fluid distributor pad. The predetermined range of time in which the sample volume of the liquid is retained by the internal reservoir is based on at least a viscosity of the liquid or a rate at which the fluid distributor pad wicks the liquid or a wicking rate of the fluid distributor pad.

By integrating the internal reservoir 120 within the rapid test device, there is a reduction/elimination of overflow of the sample, as well as droplet formation outside the top cover 105 and bottom cover 150. In addition, the integration of the internal reservoir 120 reduces/eliminates sample lost from improper absorption by the cover layer.

With continued reference to the illustrative embodiment of FIG. 2, the fluid distributor pad 125 is arranged in fluid communication with a lower surface of the internal reservoir 120. The fluid distributor pad 125 is configured to divide a portion of the sample deposition in the internal reservoir 120 substantially equally among a plurality of flow paths. In turn, the flow paths are in fluid communication of the flow lines of the lateral flow assays 130. In this embodiment, the fluid distributor pad 125 has wax defined hydrophilic channels fabricated in the same sample pad material of the lateral flow assays to enhance sample distribution into the lateral flow assays 130. By using the same material for the fluid distributor pad 125 as the sample pad of the lateral flow assays, a more effective transfer of fluid from the fluid distributor into the lateral flow assays is achieved. And by using a carefully designed wax defined channels the amount of sample retained by the fluid distributor pad 125 decreases. In addition, the design of the wax defined channels achieves a more uniform distribution under varying conditions (e.g., the multiplexed lateral flow device being tilted, dropped, etc.).

Spacer element 140 is an intermediate support layer. As shown in the illustrative embodiment of FIG. 2, the spacer element 140 is constructed of a material that is pre-treated (e.g. coated) to make the material impermeable to the liquid sample and a buffer solution. The material used to construct the spacer element in this embodiment is cardboard, but the construction is not limited to this material. For example, chipboard may be used.

At least one partitioning strip 145 is arranged to separate the lateral flow assays 130 that are housed in the area defined by the partitioning strip 145, so as to prevent cross contamination. The partitioning strip 145, along with the rest of the spacer element 140, can also serve to ensure that there is a gap between the top cover 105 and the lateral flow assays 130, to prevent contamination of the flow lines, or impedance of the flow lines, by the top cover inadvertently coming into contact with the surface of the lateral flow assays 130. There may be more than one partitioning strip 145 if the quantity of lateral flow assays 130 exceeds two. Although not shown, for example, two partitioning strips 145 can be used if there are three lateral flow assays. By permitting the use of multiple lateral flow assays that are housed in the spacer element 140, tests for multiple reagents may be performed from a single deposition sample. It is also shown in this embodiment that the partitioning strip 145 does not partition the entire area defined by the spacer element. There is an un-partitioned area for the arrangement of the fluid distributor pad 125 and the internal reservoir 120. The impermeable bottom cover 150 and the spacer element 140 combine to form a housing element (in conjunction with the top cover) for the arrangement and alignment of the internal reservoir 120, the fluid distributor pad 125 and the two or more lateral flow assays.

With continued reference to FIG. 2, strategic pressure elements 160 may be arranged to enhance contact reliability at interfaces between the sample pad 305 and conjugate pad 310 of the lateral flow assays (shown in FIG. 3), and between the conjugate pad 310 and the membrane 315 of the lateral flow assays.

Figure 3:
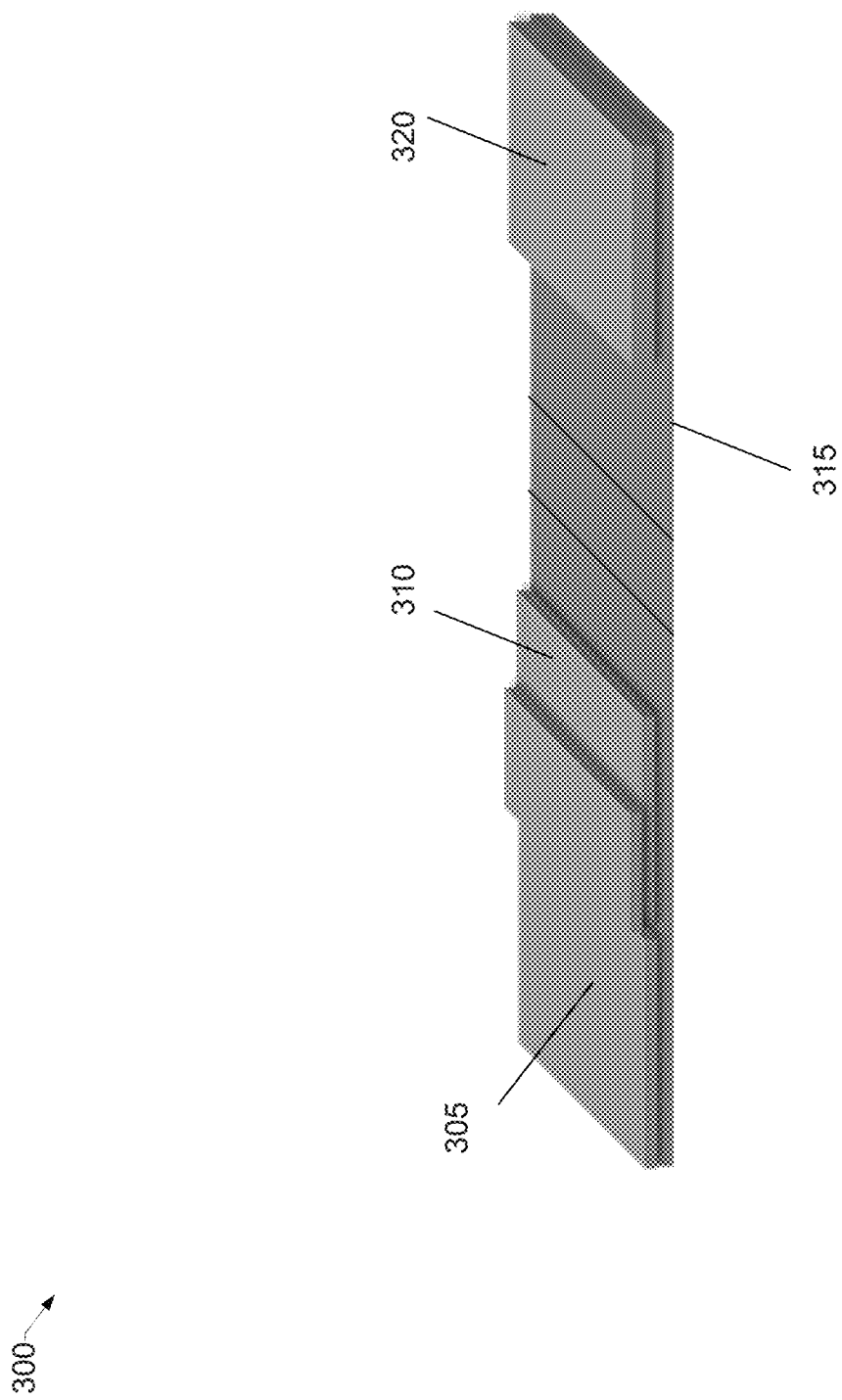
FIG. 3 is an illustration of a lateral flow assay, consistent with an illustrative embodiment.

FIG. 3 is an illustration of a lateral flow assay consistent with an illustrative embodiment. A lateral flow assay may include a sample pad/blood separator 305, a conjugate pad 310, a membrane 315 with test and control lines or other patterns, and a wicking pad 320. Typically, the flow is from the sample pad/blood separator 305 toward the wicking pad 320. The liquid is pulled by the wicking effect of the porous medium without the need for external pumps.

FIGS. 4A, 4B, 4C, and 4D are illustrations of the operation of a fluid distributor pad, consistent with an illustrative embodiment.

Figure 4B:
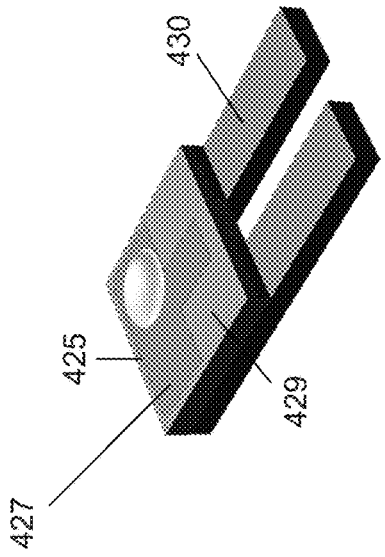
FIGS. 4A, 4B, 4C, and 4D are illustrations of the operation of a fluid distributor pad, consistent with an illustrative embodiment.
Figure 4D:
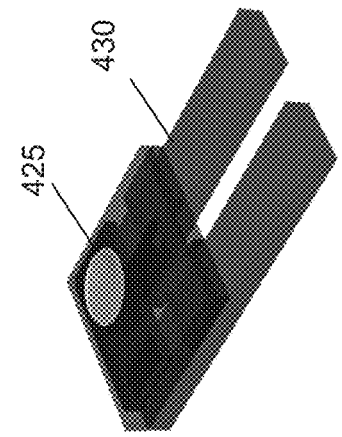
Figure 4A:
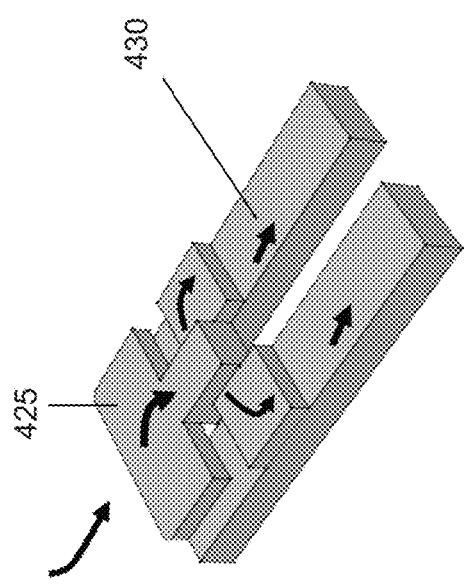

For example, at FIG. 4A, there is a fluid distributor pad 425, and it can be seen there is a flow from the interface with the reservoir through hydrophilic paper channels to a control portion, and then distribution to the lateral flow assays 430.

Reference now is made to FIG. 4A, where the arrows represent the flow direction of the sample received by the lateral flow assays 430 from the fluid distributor pad 425 as it progresses through the fluid distributor pad channels from the interface with the internal reservoir. Reference now is made to FIG. 4B, which shows at a liquid droplet that flows through the hydrophilic paper channels 427. FIG. 4B shows hydrophobic wax areas 429 used to control the flow to the lateral flow assays 430. In addition, FIG. 4D shows a semi-transparent representation of the fluid distributor pad design of FIG. 4B.

Figure 4C:
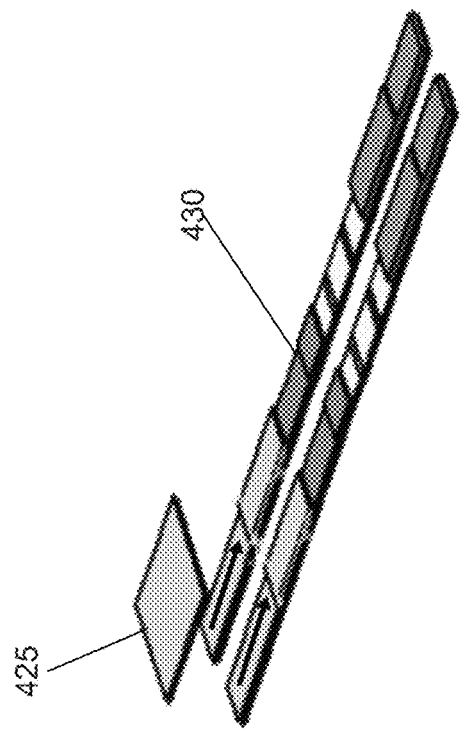

With reference to FIG. 4C now, the placement of the fluid distributor pad 425 relative to the lateral flow assays 430 is shown.

Figure 5D:
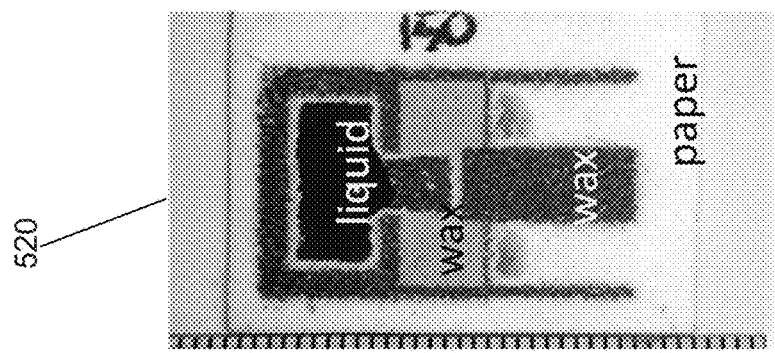
FIGS. 5A, 5B, 5C, and 5D show various constructions of wax patterns of a fluid distributor pad, consistent with illustrative embodiments.
Figure 5C:
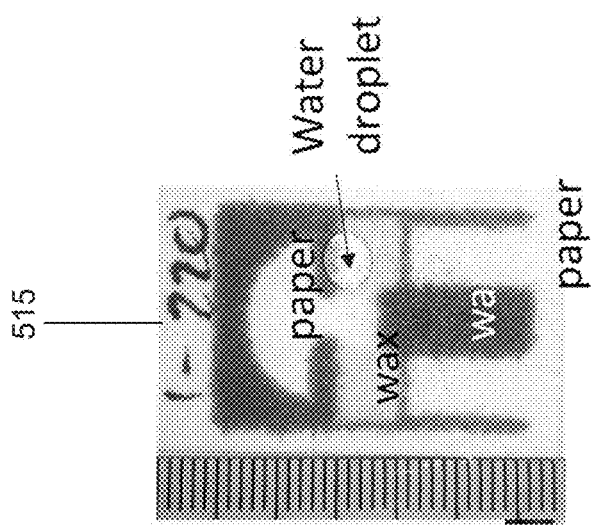
Figure 5A:
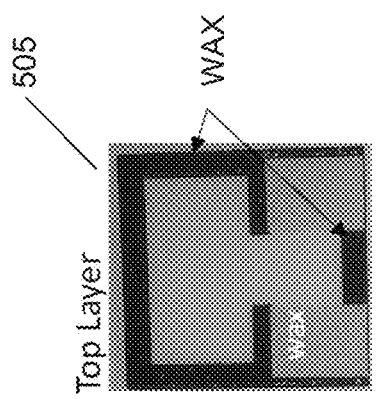
Figure 5B:
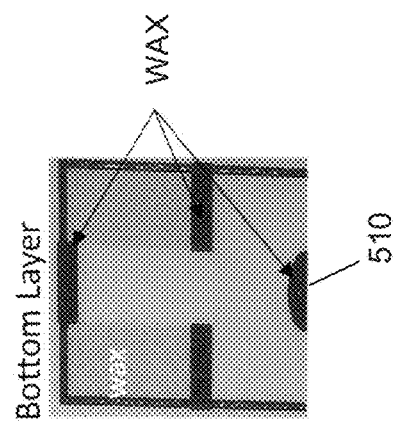

FIGS. 5A, 5B, 5C, and 5D show some of the various constructions of wax patterns of a fluid distributor pad consistent with illustrative embodiments of the present disclosure. Reference now is made to FIG. 5A, where the top layer of fluid distributor pad 505 has a wax pattern that is different than the wax pattern shown in FIG. 5B of the bottom layer 510. At manufacturing, a wax pattern is deposited on the paper sheet top and bottom surfaces by means of a wax printer or other known methods and uses a gray scale to define the channel design prior to undergoing a reflow process. The reflow process consists of applying heat to melt the wax and impregnate the thickness of the paper sheet to create hydrophobic barriers to the movement of fluid. Depending on the paper sheet thickness, some gray scale wax features only partially penetrate the thickness of the paper and can be used to create three-dimensional wax barriers, that is, on the plane and through the thickness of the paper. Referring to FIG. 5C, it is shown in 515 that a grey scale wax feature maintains hydrophobicity after reflow. With reference to FIG. 5D, as shown in 520, a custom design achieves uniform sample distribution. The custom design may take into consideration the effects of wax reflow (e.g.: spread, diffusion, penetration) in constructing the wax pattern, so that a more uniform sample distribution is achieved.

Figure 6:
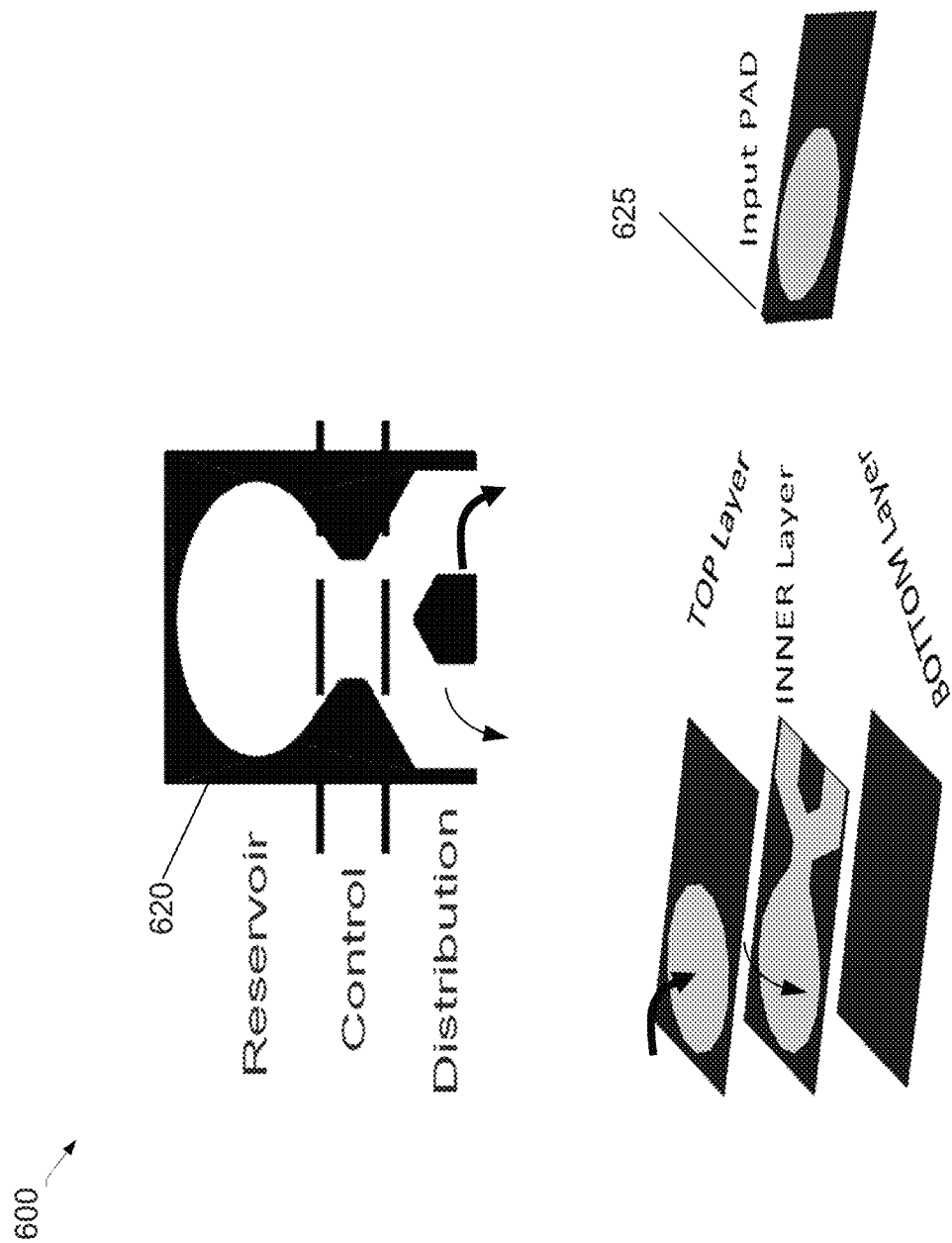
FIG. 6 shows an alternative fluid distributor pad having a horizontal structure, consistent with an illustrative embodiment.

FIG. 6 shows an alternative embodiment of a multi-layer fluid distributor pad having a horizontal structure, consistent with an illustrative embodiment. The multi-layer fluid distributor pad 625 is arranged in fluid communication with the internal reservoir 620. The multi-layer fluid distributor pad includes a top layer, an inner layer, and a bottom layer comprising a hydrophobic wax-filled area, and a hydrophilic paper channel communicating with a plurality of flow paths configured to distribute at least a portion of the sample deposition in the internal reservoir substantially equally among the plurality of flow paths. The multi-layer fluid distributor pad shown in FIG. 6 has a horizontal arrangement of the reservoir, control and distribution portions. A sample from the top layer is transferred to the inner layer and divided into hydrophilic paper channels that are in communication with the lateral flow assays.

Figure 7:
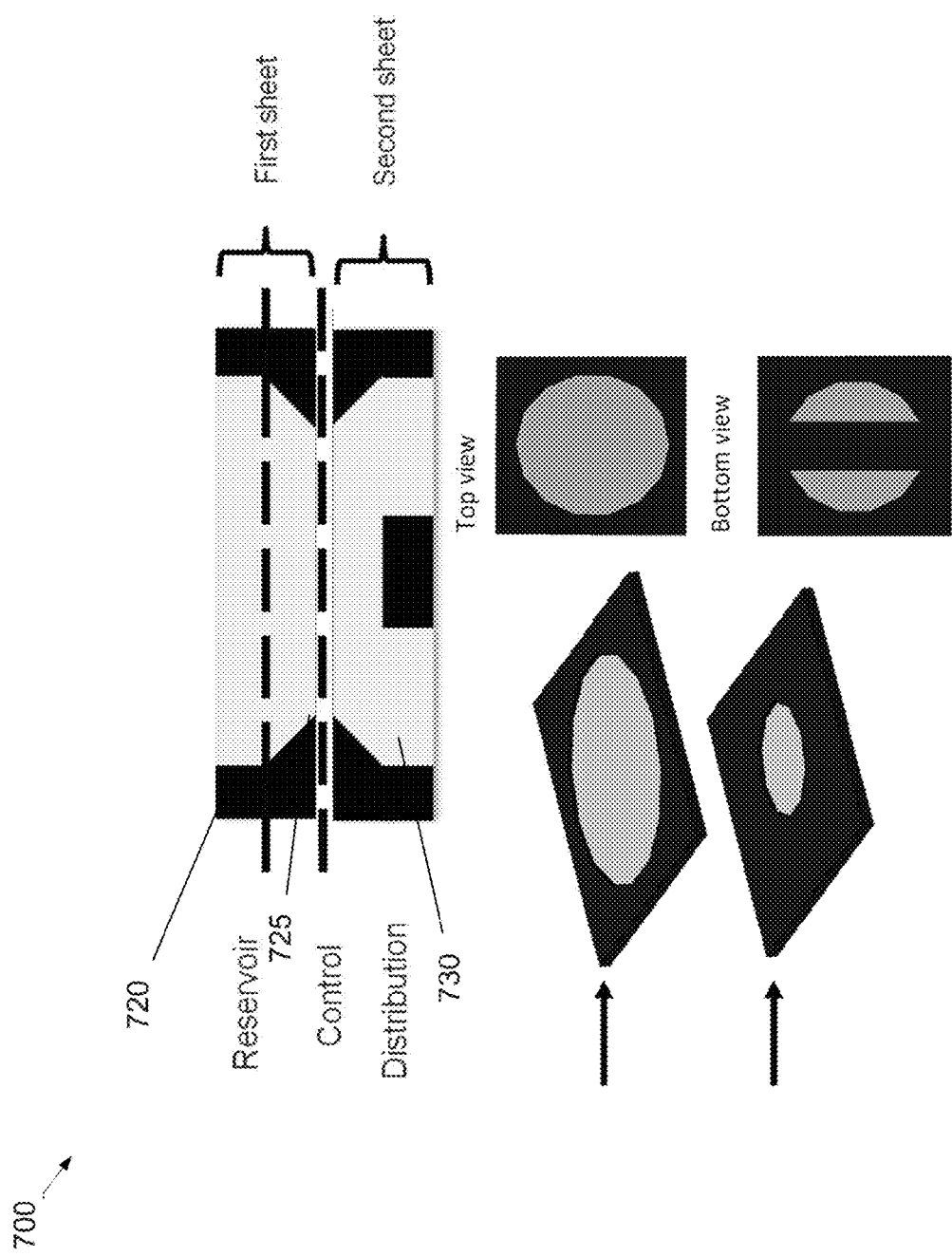
FIG. 7 shows an alternative fluid distributor pad having a vertical structure, consistent with an illustrative embodiment.

FIG. 7 shows in 700 another embodiment of an alternative fluid distributor pad having a vertical structure, consistent with an illustrative embodiment. The fluid distributor pad has a vertical arrangement of the reservoir 720, control 725 and distribution 730 portions.

Figure 8:
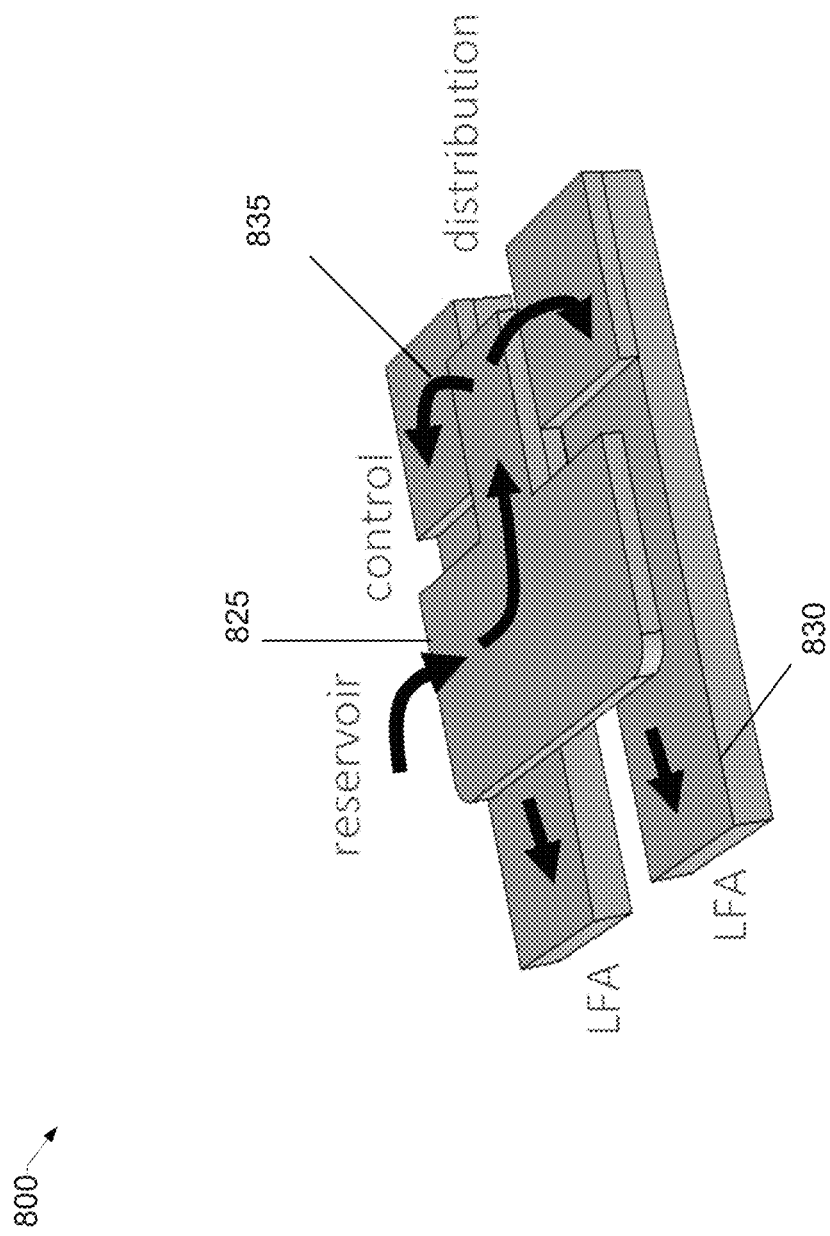
FIG. 8 shows a fluid distributor pad structure having a backward orientation, consistent with an illustrative embodiment.

FIG. 8 shows a fluid distributor pad structure 825 having a backward orientation 835, consistent with an illustrative embodiment. The term "backward" is used in reference to the distributor pad structure of FIG. 4A and because, as illustrated in FIG. 8, the flow initially moves away (e.g., backward) from the lateral flow assays. However, the flows are ultimately directed to the respective lateral flow assays 830 after being distributed. Both the forward orientation fluid distributor pad design of FIG. 4A and the backward orientation fluid distributor pad design of FIG. 8 is a type of hybrid construction, combining concepts from the vertical and horizontal structures on a single sheet of paper with different top and bottom wax patterns.

Figure 9:
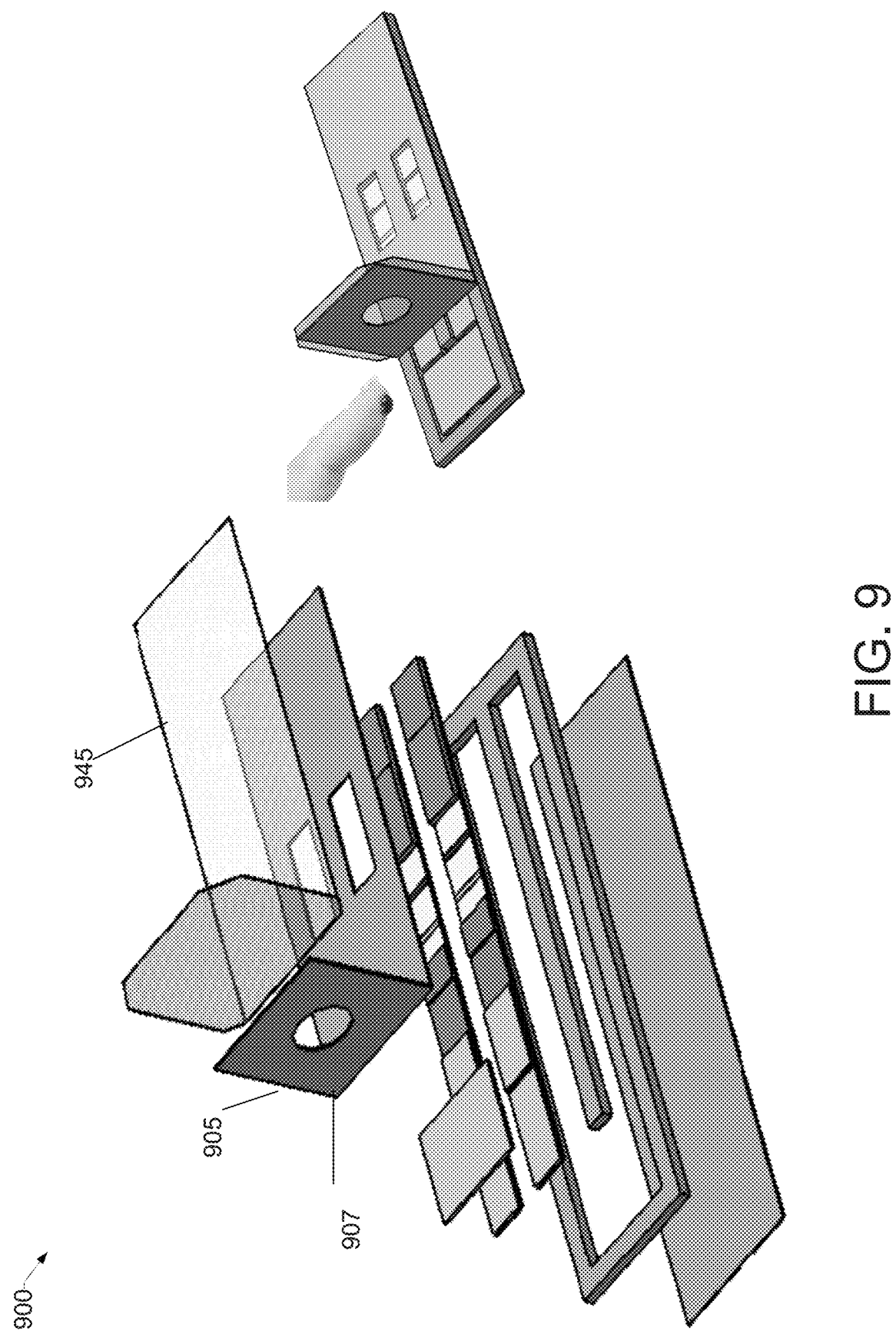
FIG. 9 shows a multiplexed lateral flow device having a direct sample collection, consistent with an illustrative embodiment.

FIG. 9 is an illustrative embodiment of a sample collection. In this case, a portion of the top cover 905 is foldable to open the area where the sample is directly collected, followed by a buffer deposition. The cover is then closed. An adhesive may be arranged around the foldable portion for entry sealing. The top cover may include a hinge portion 907 by which the portion of the top cover 905 is foldable. Lamination 945 may optionally be arranged over the top cover 905.

Figure 10B:
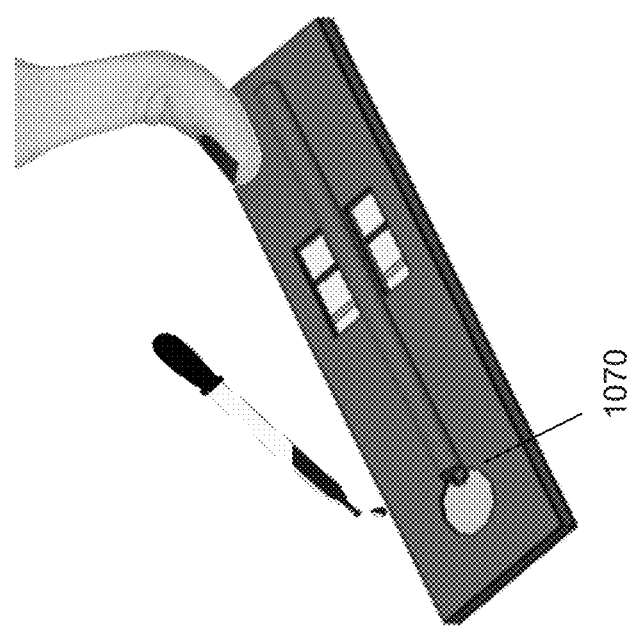
Figure 10A:
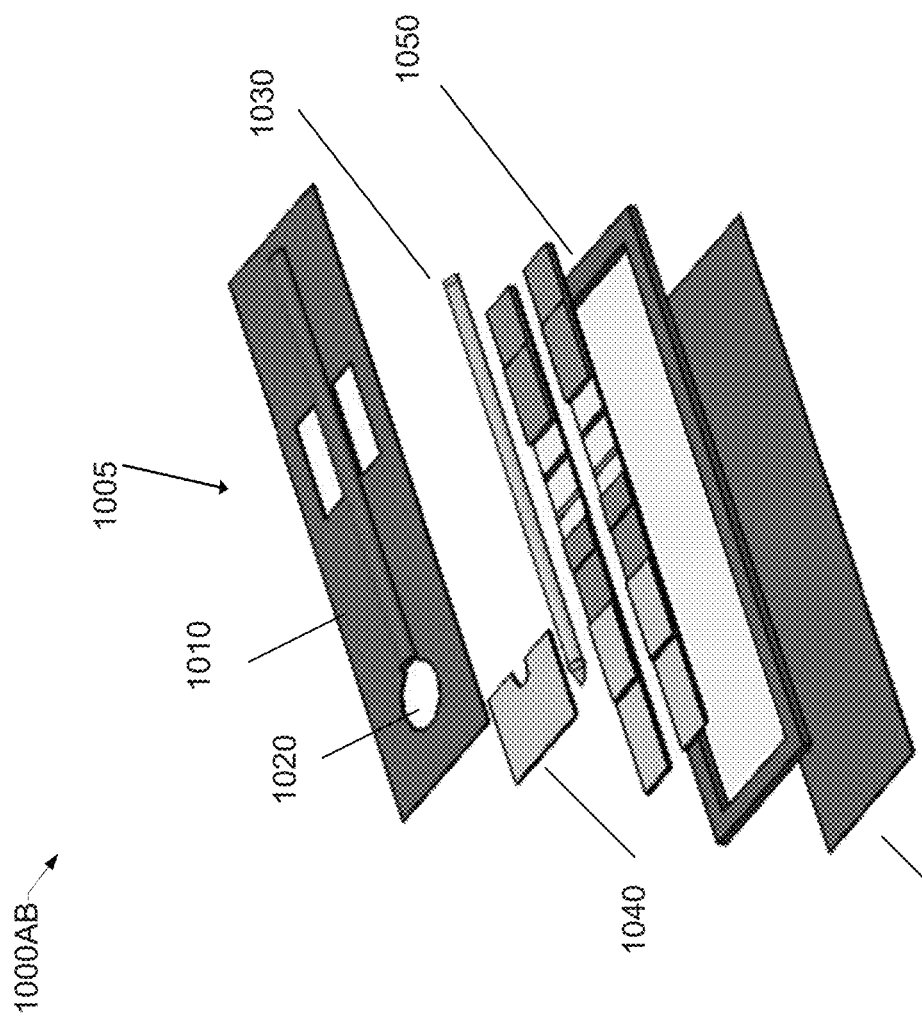

FIGS. 10A, 10B, and 10C show a multiplexed lateral device having an integrated buffer container, consistent with an illustrative embodiment.

FIGS. 10A and 10B show in 1000AB respectively, an exploded view and a perspective view of a multiplexed lateral flow device 1005. With reference to FIG. 10A, a top cover 1010 with an opening 1020 for sample deposition. An integrated buffer container 1030 is filled with, for example, a buffer/anticoagulant. A spacer element 1050 and bottom cover 1060 form part of a housing element in which the fluid distributor pad 1040 is common to two lateral flow assays. As shown in FIG. 10B, when pressure is applied to the top cover 1010, from, for example, a finger, the integrated buffer container opens and a buffer 1070 is released from into the opening area for sample deposition 1020. This construction eliminates the need to separately store, transport, and handle an external buffer that is used with the sample deposition.

FIG. 10C shows in 1000C an illustration of another integrated buffer container consistent with an illustrative embodiment. A blister 1075 is arranged in the top cover so that when pressure is applied, solution 1085 is released from the blister to the lateral flow assays 1090 (see FIG. 10A for another view of lateral flow assays). The blister 1075 may be constructed of a plastic. As shown in side view 1080, the blister 1075 may partially extrude from the top cover. In an alternative construction, the blister 1075 may be used in conjunction with a water soluble polymer film, such as, for example, polyvinyl alcohol. The time to release the solution 1085 is controlled by the polymer dissolution time.

With reference to the foregoing overview of the example architecture 100A and conceptual block, it may be helpful now to consider a high-level discussion of an example process. To that end, FIG. 11 presents an example process according to an illustrative embodiment.

Figure 11:
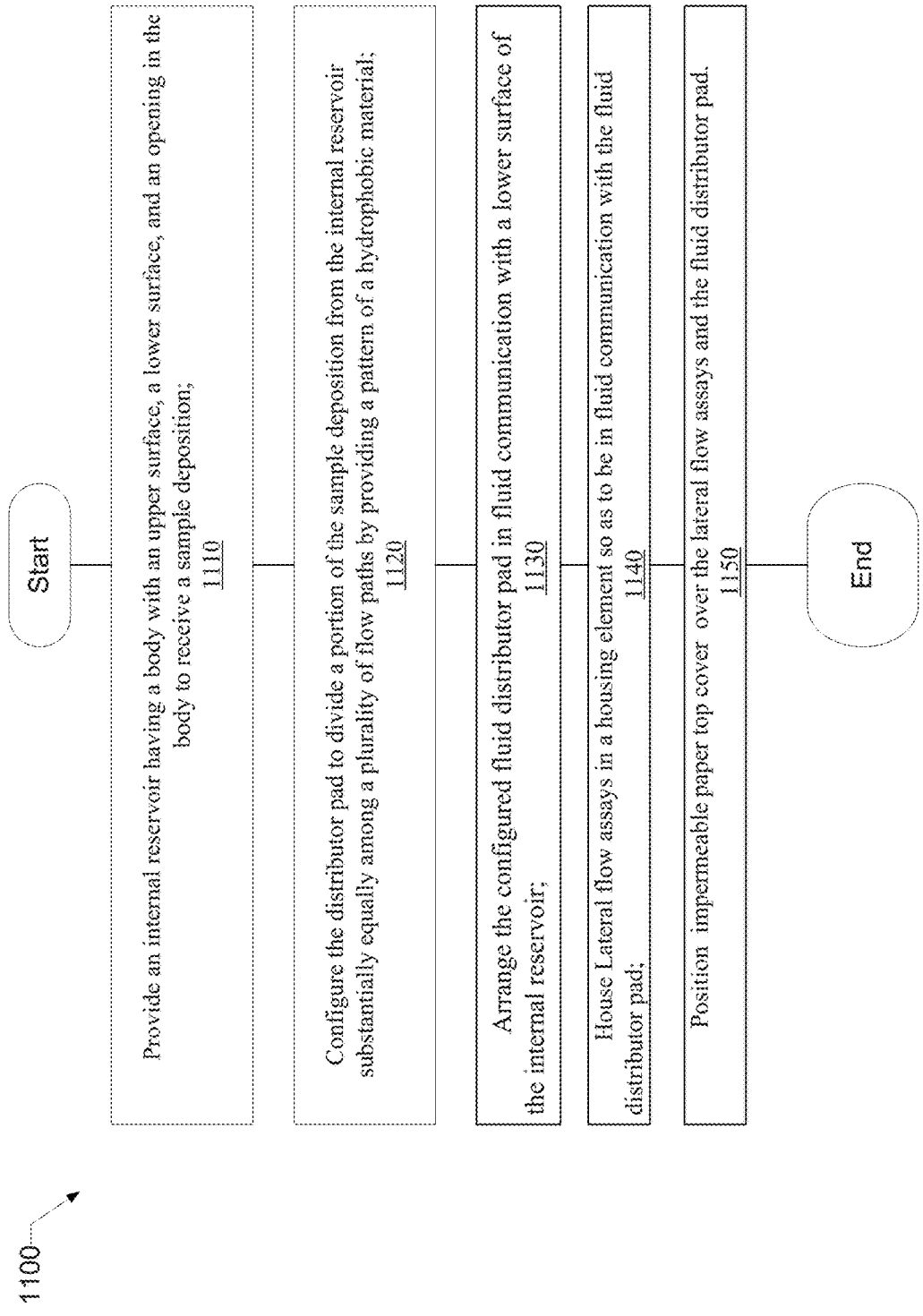
FIG. 11 is a flowchart providing an overview for a method of manufacturing a multiplexed lateral flow assay device, consistent with an illustrative embodiment.

With reference to the flowchart 1100 in the illustrative embodiment of FIG. 11, a method of manufacturing a multiplexed lateral flow device includes an operation 1110 of providing an impermeable internal reservoir having a body with an upper surface, a lower surface, and an opening in the body to receive a sample deposition.

At block 1120, the fluid distributor pad is configured to divide a portion of the sample deposition in the internal reservoir substantially equally among a plurality of flow paths by providing a pattern of a hydrophobic material on the fluid distributor pad to distribute the sample. The hydrophobic material may be, for example, a wax pattern.

At block 1130, the configured fluid distributor pad is arranged in fluid communication with a lower surface of the internal reservoir.

At block 1140, two or more lateral flow assays (having the plurality of flow paths), the fluid distributor pad and the internal reservoir are arranged in a housing element. The housing element includes an impermeable bottom cover and an impermeable spacer element. The lateral flow assays include, for example, a test result portion and a control portion for each assay test. The spacer element comprises a material that is impermeable to the sample and the buffer solution. Alternatively, the spacer element may be coated with a hydrophobic material prior to the lateral flow assays being housed therein. In addition, the spacer element is sized to provide a gap between the lateral flow assays and the impermeable top cover so the lateral flow assays are not contaminated by contact from the impermeable top cover.

At block 1150, an impermeable top cover is positioned over the housing element lodging the internal reservoir, the lateral flow assays and the distributor pad. The housing element comprising an impermeable bottom cover and an impermeable spacer element arranged between the impermeable top cover and the impermeable bottom cover. The impermeable top cover has a first window arranged over the opening of the internal reservoir, and at least a second window arranged over the test result portion and the control portion of the lateral flow assays.

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, the inventive subject matter lies in less than all features of a single disclosed embodiment. Thus, the following claims are hereby incorporated into the Detailed Description, with each claim standing on its own as a separately claimed subject matter.

What is claimed is:

1. A multiplexed lateral flow device, comprising:
   an impermeable internal reservoir having a body with an upper surface, a lower surface, and an opening in the body to receive a sample deposition;
   a fluid distributor pad arranged in fluid communication with a lower surface of the internal reservoir, the fluid distributor pad comprising a paper-based microfluidic element having a pattern of a hydrophobic material to distribute the sample deposition substantially equally among a plurality of flow paths;
   two or more lateral flow assays having a plurality of flow lines arranged in fluid communication with the plurality of flow paths of the fluid distributor pad;
   an impermeable top cover having a first window arranged over the opening of the internal reservoir, and a second window arranged over a test result of the lateral flow assays;
   an impermeable bottom cover opposing the impermeable top cover; and
   an impermeable housing element arranged between the impermeable top cover and the impermeable bottom cover;
   wherein the reservoir, the fluid distributor pad and the two or more lateral flow assays are arranged within the housing element, and
   wherein the housing element includes a spacer element configured to provide a gap between the two or more lateral flow assays and impermeable top cover.

2. The multiplexed lateral flow device according to claim 1, wherein the internal reservoir is configured to receive a sample volume of a liquid, and to retain decreasing portions of the sample volume over a predetermined range of time equal to or greater than a time during which the liquid is being wicked into the fluid distributor pad.

3. The multiplexed lateral flow device according to claim 2, wherein the predetermined range of time in which the sample volume of the liquid is retained by the internal reservoir is based on at least a viscosity of the liquid or a rate at which the fluid distributor pad wicks the liquid or a wicking rate of the fluid distributor pad.

4. The multiplexed lateral flow device according to claim 1, wherein the top cover and the bottom cover are formed of a material having a hydrophobic coating that is impermeable to a sample and a buffer solution.

5. The multiplexed lateral flow device according to claim 1, wherein
the spacer element is constructed of an impermeable material; and
the fluid distributor pad is configured to divide a portion of the sample deposition in the internal reservoir substantially equally among a plurality of flow paths.

6. The multiplexed lateral flow device according to claim 1, wherein the two or more lateral flow assays include a test result portion and a control portion for each assay test.

7. The multiplexed lateral flow device according to claim 1, further comprising a plurality of strategic pressure elements arranged between the impermeable top cover and an upper portion of the lateral flow assays.

8. The multiplexed lateral flow device according to claim 7, wherein the plurality of strategic pressure elements are laterally arranged to increase contact pressure at predetermined interfaces of the two or more lateral flow assays.

9. The multiplexed lateral flow device according to claim 1, wherein:
the internal reservoir, the spacer element, pressure elements, the top cover and the bottom cover, are made of a paper material,
the two or more lateral flow assays comprise a plurality of immuno assays respectively configured to perform, at a same time, a different assay test or a repetitive assay test, and
the spacer element includes one or more partitioning strips that isolate each of the plurality of lateral flow assays arranged in the housing element.

10. The multiplexed lateral flow device according to claim 1, wherein the housing element includes an un-partitioned area for the arrangement of the internal reservoir and the fluid distributor pad in alignment with the two or more lateral flow assays.

11. The multiplexed lateral flow device according to claim 1, wherein the fluid distributor pad comprises a single sheet of paper having wax patterns on a top of the single sheet of paper, which are different from wax patterns on a bottom of the single sheet of paper.

12. The multiplexed lateral flow device according to claim 1, configured to test for a presence of analytes of interest in bodily fluids.

13. The multiplexed lateral flow device according to claim 12, wherein the analytes include at least one of saliva, oral fluids, whole blood, blood serum, blood plasma, or urine.

14. The multiplexed lateral flow device according to claim 1, wherein the multiplexed lateral flow device includes biomarkers configured to perform diagnostic tests on one or more of HIV, syphilis, dengue, or tuberculosis.

15. The multiplexed lateral flow device according to claim 1, further comprising biomarkers configured to perform treatment monitoring tests on one or more of HIV, syphilis, dengue or tuberculosis.

* * * * *